US00PP31800P2

(12) United States Plant Patent
Winslow

(10) Patent No.: US PP31,800 P2
(45) Date of Patent: May 26, 2020

(54) ***IPOMOEA* PLANT NAMED 'BALSOTOWLIM'**

(50) Latin Name: *Ipomoea batatas*
Varietal Denomination: Balsotowlim

(71) Applicant: Ball Horticultural Company, West Chicago, IL (US)

(72) Inventor: Benjamin K. Winslow, Austin, TX (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/501,926

(22) Filed: Jul. 3, 2019

(51) Int. Cl.
*A01H 5/00* (2018.01)
*A01H 6/00* (2018.01)

(52) U.S. Cl.
USPC ..... Plt./258

(58) Field of Classification Search
USPC ..... Plt./258
CPC ..... A01H 5/00; A01H 5/02; A01H 6/00
See application file for complete search history.

*Primary Examiner* — Keith O. Robinson
(74) *Attorney, Agent, or Firm* — Audrey Charles

(57) ABSTRACT

A new and distinct cultivar of an ornamental *Ipomoea* plant named 'Balsotowlim', characterized by its medium lime-green colored foliage, and vigorous, climbing growth habit, is disclosed.

1 Drawing Sheet

Latin name of genus and species of plant claimed: *Ipomoea batatas.*

Variety denomination: 'Balsotowlim'.

BACKGROUND OF THE INVENTION

The present invention relates to a new and distinct cultivar of *Ipomoea* plant botanically known as *Ipomoea batatas* and hereinafter referred to by the cultivar name 'Balsotowlim'.

The new cultivar originated in a controlled breeding program in Arroyo Grande, Calif. during January 2015. The objective of the breeding program was the development of ornamental *Ipomoea* cultivars with a vigorous, climbing habit.

The new ornamental *Ipomoea* cultivar is the result of cross-pollination. The female (seed) parent of the new cultivar is the proprietary *Ipomoea batatas* breeding selection coded 098-001, not patented, characterized by its light lime-green colored foliage and moderately vigorous, spreading growth habit. The male (pollen) parent of the new cultivar is 'Okinawa Purple', not patented, characterized by its medium blue-green colored foliage and vigorous, climbing growth habit. The new cultivar was discovered and selected as a single plant within the progeny of the above stated cross-pollination during May 2015 in a controlled environment in Arroyo Grande, Calif.

Asexual reproduction of the new cultivar by terminal stem cuttings since May 2015 in Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsotowlim' as a new and distinct cultivar of *Ipomoea* plant:

1. Medium lime-green colored foliage; and
2. Vigorous, climbing growth habit.

Plants of the new cultivar differ from plants of the female parent primarily in having a climbing growth habit. Plants of the new cultivar differ from plants of the male parent primarily in having a lighter and lime green-colored foliage.

Of the many commercially available ornamental *Ipomoea* cultivars, the most similar in comparison to the new cultivar is SolarPower Lime 'Balsolalimli', U.S. Plant Pat. No. 29,536. However, in side-by-side comparison, plants of the new cultivar differ from plants of 'Balsolalimli' in at least the following characteristics:

1. Plants of the new cultivar have a more vigorous, climbing growth habit than plants of 'Balsolalimli'; and
2. Plants of the new cultivar have a leaf shape that is more shallowly lobed than plants of 'Balsolalimli'.

The new cultivar can also be compared to formerly commercially available SolarTower Lime 'Balsotowime', U.S. Plant Pat. No. 29,510. However, in side-by-side comparison, plants of the new cultivar differ from plants of 'Balsotowime' in at least the following characteristics:

1. Plants of the new cultivar are taller and wider than plants of 'Balsotowime'; and
2. Plants of the new cultivar have more branches per plant than plants of 'Balsotowime'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs may differ slightly from the color values cited in the detailed description, which accurately describes the colors of 'Balsotowlim'. The plants were approximately 3 months old and grown in 6-inch pots for approximately 7 weeks in a greenhouse in West Chicago, Ill.

DETAILED BOTANICAL DESCRIPTION

Figure 1:
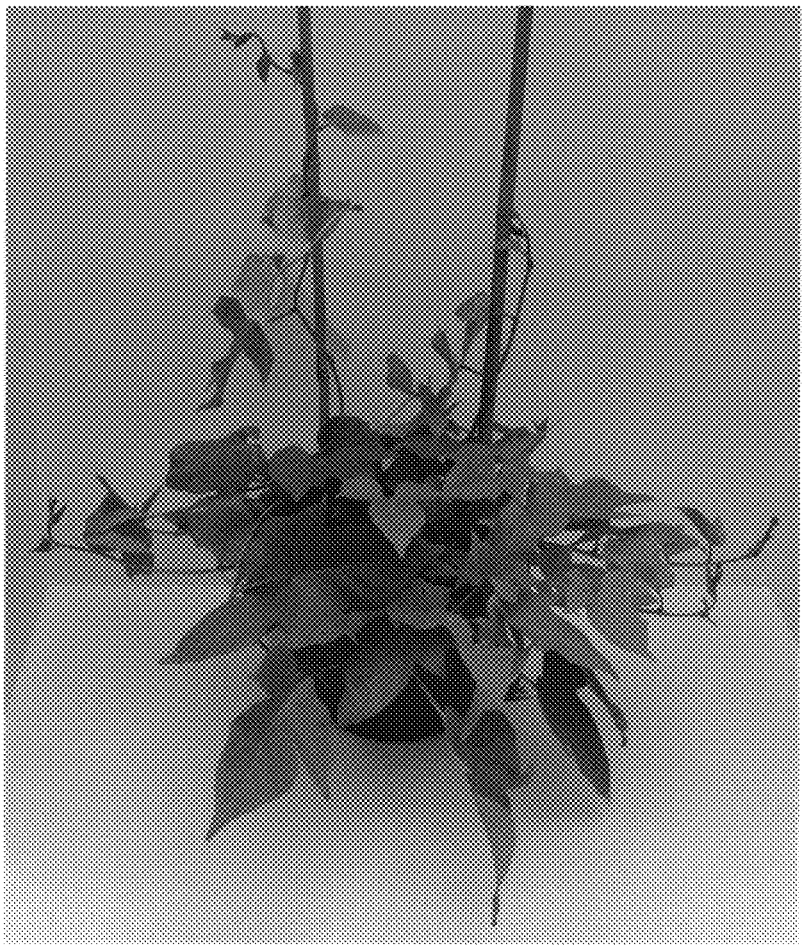
FIG. 1 illustrates a side view of the overall growth and habit of 'Balsotowlim'.
Figure 2:
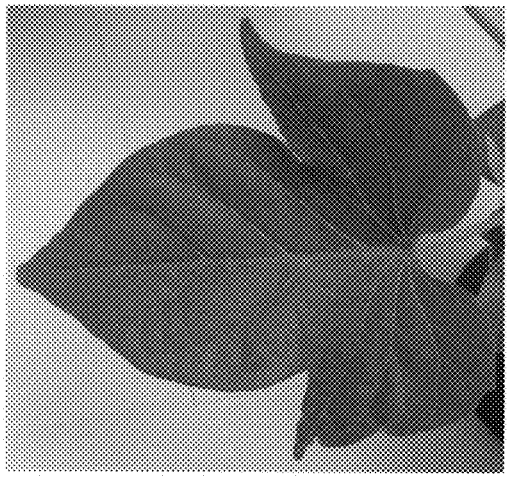
FIG. 2 illustrates a close-up view of an individual leaf of 'Balsotowlim'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2017 under natural light conditions in West Chicago, Ill.

The following descriptions and measurements describe approximately 3-month old plants produced from cuttings from stock plants and grown in a glass-covered greenhouse under conditions comparable to those used in commercial practice. The plants were grown in West Chicago, Ill. in 6-inch pots for approximately 7 weeks utilizing a soilless growth medium. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Ipomoea batatas* 'Balsotowlim'.

Parentage:

*Female parent.*—Proprietary *Ipomoea batatas* breeding selection coded 098-001, not patented.

*Male parent.*—'Okinawa Purple', not patented.

Propagation:

*Type cutting.*—Terminal stem.

*Time to initiate roots.*—Approximately 3 to 4 days.

*Time to produce a rooted cutting.*—Approximately 21 to 28 days.

*Root description.*—Fibrous, medium thickness.

*Rooting habit.*—Freely branching.

*Storage root description.*—Not available, storage root formation not observed to date.

Plant description:

*Commercial crop time.*—Approximately 4 to 5 weeks from a rooted cutting to finish in a 10 cm pot.

*Growth habit and general appearance.*—Vigorous, climbing growth habit.

*Size.*—Height (as supported for climbing): Approximately 42.0 cm. Height (unsupported for climbing): Approximately 15.0 cm. Length (unsupported for climbing): Approximately 97.0 cm. Width: Approximately 47.0 cm.

*Branching habit.*—Freely branching, pinching not needed, but enhances basal branching. Quantity of main branches per plant: Approximately 5.

*Branch.*—Shape: Round. Strength: Strong, flexible. Length: Approximately 36.0 cm. Diameter: Approximately 4.0 mm. Length of central internode: Approximately 5.0 cm. Texture: Sparsely pubescent. Color of young stems: 145A to 145B. Color of mature stems: 145A to 145B, occasionally tinted with N187A.

Foliage description:

*General description.*—Quantity of leaves per main branch: Approximately 7. Fragrance: None detected. Form: Simple. Arrangement: Alternate, spiral.

*Leaves.*—Shape: Cordate with two shallow lateral lobes, that become slightly deeper with plant age. Margin: Entire. Apex: Acuminate. Base: Cordate. Venation pattern: Palmate with arcuate venation in the center lamina. Length of mature leaf: Approximately 12.0 cm. Width of mature leaf: Approximately 8.0 cm. Texture of upper and lower surfaces: Glabrous. Color of upper surface of young foliage: Closest to but more green than 145A with slightly darker venation and a faint margin of N187A. Color of lower surface of young foliage: Closest to 147C with venation of 145C and a faint margin of N187A. Color of upper surface of mature foliage: Closest to 144D with venation of 145A. Color of lower surface of mature foliage: Closest to 147D with venation of 145D.

*Petiole.*—Length: Approximately 8.0 cm. Diameter: Approximately 3.0 mm. Texture: Glabrous. Color: 145A to 145B with a faint tint of N187A with 187A at leaf attachment.

Flowering description: Flowers not observed to date. The new ornamental *Ipomoea* cultivar is grown as a foliage plant and is not grown under conditions that are conducive to flower production.

Disease and pest resistance: Resistance to pathogens and pests common to *Ipomoea* has not been observed.

What is claimed is:

1. A new and distinct cultivar of an ornamental *Ipomoea* plant named 'Balsotowlim' substantially as herein illustrated and described.

* * * * *